United States Patent
Ueno et al.

(10) Patent No.: US 6,863,737 B2
(45) Date of Patent: Mar. 8, 2005

(54) CRYSTALLINE MIXTURE SOLID CONTAINING MALTITOL AND PREPARATION THEREFOR

(75) Inventors: Ryuzo Ueno, Nishinomiya (JP); Akihiko Tabata, Kawanishi (JP); Junya Honda, Nishinomiya (JP); Yojiro Furukawa, Itami (JP)

(73) Assignee: Kabushiki Kaisha Ueno Seiyaku Oyo Kenkyusho, Osaka (JP)

( * ) Notice: Subject to any disclaimer, the term of this patent is extended or adjusted under 35 U.S.C. 154(b) by 231 days.

(21) Appl. No.: 10/048,585

(22) PCT Filed: Jul. 3, 2001

(86) PCT No.: PCT/JP01/05753

§ 371 (c)(1),
(2), (4) Date: Feb. 1, 2002

(87) PCT Pub. No.: WO02/02581

PCT Pub. Date: Jan. 10, 2002

(65) Prior Publication Data

US 2003/0188739 A1 Oct. 9, 2003

(30) Foreign Application Priority Data

Jul. 5, 2000 (JP) ........................................ 2000-204142

(51) Int. Cl.⁷ ........................... C13F 1/02; C08B 30/00; C07H 1/00; C07H 1/06; C13K 5/00
(52) U.S. Cl. ............................. 127/58; 127/29; 127/30; 127/60; 127/61; 536/1.11; 536/123.13; 536/124; 536/127
(58) Field of Search .............................. 127/29, 30, 58, 127/60, 61; 536/1.11, 123.13, 124, 127

(56) References Cited

U.S. PATENT DOCUMENTS

| 4,408,041 A | 10/1983 | Hirao et al. | |
| 4,846,139 A | 7/1989 | Devos et al. | 127/40 |
| 4,849,023 A | 7/1989 | Devos et al. | 127/40 |
| 5,304,388 A * | 4/1994 | Ueno et al. | 426/658 |
| 5,354,856 A | 10/1994 | Kawashima et al. | 536/127 |
| 5,583,215 A | 12/1996 | Kawashima et al. | 536/127 |

FOREIGN PATENT DOCUMENTS

| EP | 0-491953 A1 | 7/1992 | ........... C07H/15/04 |
| EP | 0-561585 A1 | 9/1993 | ........... C07H/15/04 |
| EP | 0 735 042 | 10/1996 | |
| EP | 0-937733 A2 | 8/1999 | ........... C07H/15/04 |
| EP | 1300414 * | 4/2003 | ........... C07H/15/04 |
| JP | 58-158145 | 9/1983 | ........... A23L/1/09 |
| JP | 61-180795 A | 8/1986 | ........... C07H/3/00 |
| JP | 63-116673 | 5/1988 | ........... A23L/1/325 |
| JP | 1-179700 | 7/1989 | |
| JP | 62-11599 | 3/1990 | ........... C07H/15/04 |
| JP | 06/234786 | 8/1994 | ........... C07H/15/04 |
| JP | 7-14953 B2 | 2/1995 | ........... C07H/15/04 |

* cited by examiner

Primary Examiner—Mark L. Bell
Assistant Examiner—Patricia L. Hailey
(74) Attorney, Agent, or Firm—Sherman & Shalloway

(57) ABSTRACT

A crystalline mixture solid containing maltitol having an oil absorptivity of 0.1 to 6.9 wt % and a bulk density of 0.60 to 0.75 g/cc when it is ground and classified to ensure that at least 70 wt % of the obtained particles should have a particle size of 16 to 50 mesh and a process for producing a crystalline mixture solid containing maltitol, comprising introducing air bubbles into a maltitol aqueous solution. According to this process, a crystalline mixture solid containing maltitol having high solubility and almost no moisture absorption is produced at a high work efficiency and a low cost in a short period of time.

15 Claims, No Drawings

CRYSTALLINE MIXTURE SOLID CONTAINING MALTITOL AND PREPARATION THEREFOR

FIELD OF THE INVENTION

The present invention relates to a crystalline mixture solid containing maltitol and to a production process therefor.

PRIOR ART

Since maltitol is hardly digested and absorbed in a digestive organ and rarely fermented by oral bacteria, it is used in low-calorie foods, diet foods, little cariogenic foods and sweetening agents for diabetics and the like. However, as a maltitol dried product is remarkably moisture absorptive, deliquescent and hardly powdered, it is very difficult to handle.

To solve this problem, there have been proposed many technologies for crystallizing or powdering maltitol. For example, JP-B 3-7349 (the term "JP-B" as used herein means an "examined Japanese patent publication") proposes a technology for commercializing maltitol by adjusting the water content of a high-concentration maltitol solution to 2 to 15 wt %, adding a seed crystal to this solution, gradually cooling the resulting solution to solidify maltitol, roughly grinding this solidified product as required, drying and grinding it to a desired particle diameter. In this technology, a 70% aqueous solution of maltitol is concentrated to a water content of 10%, maltitol powders are added to this concentrated solution, and the resulting solution is cooled from 90° C. to normal temperature in about 20 hours to be solidified.

JP-B 1-47140 discloses a technology for obtaining granular maltitol by placing a concentrated solution of reduced maltose in a tray, adding a crystal, fully kneading and keeping warm the resulting solution to promote crystallization in order to obtain plasticity, extruding the product from pores, cooling and cutting the extruded product with an edged tool.

JP-B 7-14953 discloses a process for producing a crystalline mixture solid containing maltitol by continuously supplying a maltitol aqueous solution into an extruder having a slender cooling/kneading zone, cooling and kneading it in the presence of a seed crystal to form a maltitol magma, and continuously extruding it from an extrusion nozzle.

The above processes which make use of a seed crystal are now mainly used to produce a crystalline mixture solid containing maltitol because of the production ease of a crystalline mixture solid containing maltitol. However, as the amount of a seed crystal added must be increased to improve the production speed and part of the produced crystalline mixture solid containing maltitol is recycled in the production processes which make use of the seed crystal, the processes involve such a problem that the production efficiency is low.

Meanwhile, JP-B 2-11599 and JP-A 61-180795 (the term "JP-A" as used herein means an "unexamined published Japanese patent application"), for example, propose another production process in which maltitol is produced by hydrogenating maltose, its purity is increased by chromatography and maltitol crystals are separated from this concentrated solution.

JP-A 6-234786 discloses a process for continuously producing a maltitol slurry by continuously introducing a maltitol aqueous solution into a vessel and stirring.

SUMMARY OF THE INVENTION

It is an object of the present invention to provide a novel crystalline mixture solid containing maltitol which has eliminated the above physical problems of prior art maltitol.

It is another object of the present invention to provide a novel crystalline mixture solid containing maltitol which has high solubility and almost no moisture absorption.

It is still another object of the present invention to provide a process for producing the crystalline mixture solid containing maltitol of the present invention, which has improved production efficiency.

It is a further object of the present invention to provide a process for producing a crystalline mixture solid containing maltitol, which is capable of producing a crystalline mixture solid containing maltitol at a high work efficiency and a low cost in a short period of time.

Other objects and advantages of the present invention will become apparent from the following description.

According to the present invention, firstly, the above objects and advantages of the present invention are attained by a crystalline mixture solid containing maltitol which has an oil absorptivity of 0.1 to 6.9 wt % and a bulk density of 0.60 to 0.85 g/cc when it is ground and classified to ensure that at least 70 wt % of the obtained particles should have a particle size of 16 to 50 mesh.

Secondly, the above objects and advantages of the present invention are attained by a process for producing a crystalline mixture solid containing maltitol, comprising dispersing air bubbles in a maltitol aqueous solution, supplying the resulting aqueous solution into a kneader to form a plastic mass and grinding the mass (may be referred to as "first production process" hereinafter).

Thirdly, the above objects and advantages of the present invention are attained by a process for producing a crystalline mixture solid containing maltitol, comprising continuously supplying a maltitol aqueous solution containing air bubbles dispersed therein into an extruder having a slender kneading/cooling zone to knead and cool it to form a maltitol magma and continuously extruding the magma (may be referred to as "second production process" hereinafter).

In the fourth place, the above objects and advantages of the present invention are attained by a process for producing a crystalline mixture solid containing maltitol, comprising supplying a maltitol aqueous solution into a kneader, kneading while air is contained in the solution to disperse air bubbles, keeping kneading and cooling the resulting solution to form a plastic mass and grinding the mass (may be referred to as "third production process" hereinafter).

Finally, the above objects and advantages of the present invention are attained by a process for producing a crystalline mixture solid containing maltitol, comprising continuously supplying a maltitol aqueous solution into an extruder having a slender cooling/kneading zone, kneading while air is contained in the solution to disperse air bubbles, keeping kneading and cooling the resulting solution to form a maltitol magma and continuously extruding the magma (may be referred to as "fourth production process" hereinafter).

The present invention will be described in detail hereinbelow.

DETAILED DESCRIPTION OF THE PREFERRED EMBODIMENTS

The crystalline mixture solid containing maltitol of the present invention has an oil absorptivity of 0.1 to 6.9 wt % and a bulk density of 0.60 to 0.85 g/cc when it is ground and classified to ensure that at least 70 wt % of the obtained particles should have a particle size of 16 to 50 mesh.

The oil absorptivity when at least 70 wt % of the particles have a particle size of 16 to 50 mesh is 0.1 to 6.9 wt %, preferably 0.5 to 4.9 wt % more preferably 2.0 to 4.9 wt %.

The bulk density when at least 70 wt % of the particles have a particle size of 16 to 50 mesh is preferably 0.60 to 0.85 g/cc. The maltitol content of the crystalline mixture solid containing maltitol of the present invention is preferably 80 to 99 wt %.

The crystalline mixture solid containing maltitol of the present invention has the above characteristic properties and is therefore excellent in solubility. In spite of this, it has almost no moisture absorption.

The crystalline mixture solid containing maltitol of the present invention is produced by dispersing air bubbles in a maltitol aqueous solution and supplying the resulting solution into a kneader to knead and cool it according to the first production process, or by supplying a maltitol aqueous solution into a kneader, kneading while air is contained in the solution in the kneader to disperse air bubbles and knead and cool the resulting solution at the same time according to the third production process.

That is, the gist of the present invention is to crystallize maltitol by providing shear force to the maltitol aqueous solution in the presence of air bubbles.

The above maltitol aqueous solution as the starting material preferably has a solid content of 85 to 99 wt %, preferably 90 to 99 wt % and a maltitol purity of 80 wt % or more, preferably 80 to 99 wt %, more preferably 85 to 99 wt %. The above maltitol aqueous solution as the starting material contains substantially no maltitol crystals.

In the first production process, to disperse air bubbles in the maltitol aqueous solution, a commonly used stirrer may be used to stir the aqueous solution. At this point, it is preferred to stir the aqueous solution by supplying air into the aqueous solution from a vent pipe such as a sparger from an air generator such as a compressor. The thus prepared maltitol aqueous solution contains air bubbles in an amount of 0.5 to 20 cc, more preferably 1 to 9 cc based on 100 g of the aqueous solution. The air bubbles are preferably as big as 0.5 to 200 μm, more preferably 1 to 100 μm. Since the air bubbles are thus dispersed, the stirring time and stirring speed of the aqueous solution differ according to the concentration and temperature of the aqueous solution and the type of the stirrer. For example, when a 95% aqueous solution of maltitol having a temperature of 110° C. is to be stirred using a high-speed homomixer (Type-M of Tokushu Kiki Kogyo Co., Ltd.), it may be stirred at a stirring speed of 8,000 rpm for about 2 minutes. At this point, air bubbles are fully dispersed in the maltitol aqueous solution.

The thus obtained maltitol aqueous solution containing air bubbles fully dispersed therein is supplied into a kneader and preferably pressurized to provide shear force in order to prevent the air bubbles from substantially being removed from the aqueous solution, thereby producing the crystalline mixture solid containing maltitol of the present invention in accordance with the first production process.

The temperature when the raw material is supplied into the kneader is preferably about 50 to 110° C. in consideration of the fact that it is easier to handle when its fluidity is higher and control ease for the formation of a magma.

According to the third production process, it is possible to produce the crystalline mixture solid containing maltitol of the present invention without dispersing air bubbles in the maltitol aqueous solution in advance as described above. In this case, a sheer maltitol aqueous solution is used as the raw material, supplied into the kneader and kneaded while air is contained in the solution in the kneader to include and fully disperse air bubbles, and the resulting solution is kneaded and cooled to produce the crystalline mixture solid containing maltitol of the present invention. The preferred content and size of the air bubbles are the same as in the first production process.

The temperature when the raw material is supplied into the kneader is preferably about 80 to 110° C. in consideration of inclusion ease and dispersion ease of air bubbles in the kneader.

The cooling portion for forming a plastic mass may be adjusted to a temperature at which the generated heat of crystallization can be removed, preferably 90° C. or less, more preferably 50° C. or less.

Although the feed rate of the raw material differs according to the type and capacity of the used kneader, it is preferably 2 to 50 kg/hr when the KRC kneader (2S) of Kurimoto, Ltd. is used.

The obtained crystalline mixture solid composition can be made powdery by grinding or granular by granulation. Methods for grinding and granulation are not particularly limited and a commonly used grinder and granulator may be used. The obtained powder or granule may be dried by a commonly used drying method or sifted as required. When it is dried, airborne drying, fluidized bed drying, vacuum drying and tray drying all of which are generally used may be employed.

In the second production process and the fourth production process, an extruder having a slender cooling/kneading zone is used.

The extruder is not limited to a particular type, for example, an open or closed type, or a batch or continuous type, if it can knead and cool at the same time. Preferably, it can extrude from an exhaust port continuously after kneading and cooling. Examples of the kneader include an extruder, continuous kneader, mixtron and kneadex. Out of these, an extruder is preferred. Examples of the extruder include the KRC kneader (of Kurimoto, Ltd.), double-screw extruder for foods (of Nippon Steel Co., Ltd.) and double-screw cooking extruder (of W & P Co., Ltd. of Germany).

When the magma is to be extruded from a continuous type extruder, the shape of the magma may be arbitrary, for example noodle-like, ribbon-like, rod-like or plate-like shape. In consideration of the subsequent steps such as cooling and grinding, it is preferably extruded in a noodle-like or ribbon-like shape. A punching plate provided at the exhaust port preferably has a pore diameter of 2 to 5 mm and a porosity of 10 to 40%.

The cooling method is not particularly limited but the magma extruded from the extruder may be directly exposed to cool air, left at room temperature or cooled to room temperature with cool air on a metal net belt.

According to the above process, a powdery or granular crystalline mixture solid containing maltitol which does not require a drying step, is easy to handle, readily soluble and rarely moisture absorptive and has high quality can be obtained at a low cost in a short period of time.

The preparation method of the maltitol aqueous solution, the content and size of the air bubbles and the grinding and granulation of the obtained crystalline mixture solid in the second and fourth production processes are the same as in the first and third production processes. As for what are not described herein of the second and fourth production processes, it should be understood that the above descriptions of the first and third production processes are applied to the second and fourth production processes directly or with modifications obvious to one of ordinary skill in the art.

The following examples and comparative examples are given to further illustrate the present invention.

EXAMPLES

The following physical property values in the examples were measured as follows.

Oil Absorptivity (wt %)

15 g of a sample and an appropriate amount of castor oil were mixed together and left for 5 minutes, an oil fraction which was not retained in the sample was removed by a centrifugal machine having a60M net stretched thereon (1300 G, 10 minutes), and the weight (A) of the sample containing the residual oil was measured. The oil absorptivity was calculated from this value based on the following equation.

oil absorptivity $(wt\ \%) = (A-15)/15 \times 100$

Bulk Density (g/cc)

This was measured using the PT-N powder tester (Hosokawa Micron Co., Ltd.) (180 times of tapping).

Melting Point (° C.)

The crystalline mixture solid containing maltitol was dried at normal temperature under vacuum for 1 hour, placed in a sealed sample container (made from Ag, 15 µl) and measured for its melting point using a differential scanning thermometer (DSC6200: Seiko Instruments Co., Ltd.) at a temperature range of 30 to 200° C. and a temperature elevation rate of 4° C./min.

Content (cc/100 g) and Size of Air Bubbles

The maltitol aqueous solution containing air bubbles dispersed therein was placed in a 100 ml female cylinder to measure its density immediately (volume/weight). At the same time, the density of a control containing no air bubbles and having the same temperature was measured. The difference between the inverse numbers of the obtained values was taken as the content of the air bubbles.

The size of the air bubbles was measured by the observation of a maltitol aqueous solution containing air bubbles dispersed therein through a microscope at a magnification of ×450.

Example 1

A maltitol aqueous solution (maltitol purity=90 wt %, solid content=95 wt %, 110° C.) containing air bubbles dispersed therein was prepared by high-speed stirring (8,000 rpm) with a homomixer (Type-M of Tokushu Kika Kogyo Co., Ltd.) while air was blown into the aqueous solution. When 700 g of this maltitol aqueous solution was injected into a 2-liter batch kneader (twin armed, 30 to 40 rpm, jacket temperature=90° C.) and kept stirred, a plastic mass (85° C. at this point) was formed in 16 minutes and became powdery in 24 minutes. The obtained powders were sifted to obtain powders having a particle size of 16 to 50 mesh which were then used for the measurement of oil absorptivity, bulk density (apparent specific gravity) and melting point. The results are shown in Table 1.

Comparative Example 1

140 g of a maltitol aqueous solution (maltitol purity=90 wt %, solid content=95 wt %, 116° C.) was placed in a 2-liter separable flask and kept in a bath heated at 90° C. while it was stirred at a low speed with two pitched puddles. However, maltitol crystals were not formed after the passage of 25 minutes (the temperature of the solution was 88° C.).

Example 2

A maltitol aqueous solution (purity of maltitol=90 wt %, solid content=90 wt %, 110° C.) into which air bubbles were continuously dispersed by a line mixer (7-E line mixer of Tokushu Kika Kogyo Co., Ltd.) was continuously supplied into a continuous kneader having a slender kneading/cooling zone (KRC kneader S-2 of Kurimoto, Ltd., 60 rpm, jacket temperature=70° C.) at a rate of 5 kg/hr and kept kneaded and cooled. A noodle-like solid was discharged from a punching plate at the outlet. This was cooled and ground to obtain a high-quality crystalline mixture solid containing maltitol.

Test Example

Air dispersion by the line mixer in Example 2 was carried out under the following conditions. That is, the maltitol aqueous solution (120° C.) was stirred by the line mixer at 6,000 rpm while compressed air (about 2 kg/cm$^3$) was supplied into the aqueous solution by a compressor to uniformly disperse air in the solution.

The amount of air in the maltitol aqueous solution containing air bubbles finely and uniformly dispersed therein was 1.2 cc/100 g. When this solution was observed through a microscope and the sizes of arbitrary 106 air bubbles were measured, the average size was 18.2 µm (standard deviation of 18.3 µm, maximum=69 µm, minimum=1.2 µm).

Example 3

A maltitol aqueous solution (maltitol purity=90 wt %, solid content=95 wt %, 110° C.) was continuously supplied into a continuous kneader having a slender kneading/cooling zone (KRC kneader S-2 of Kurimoto, Ltd., 60 rpm, jacket temperature=70° C.) at a rate of 5 kg/hr and air was supplied into the kneader by a compressor at the same time to knead the solution by stirring with a kneader puddle while air was contained in the solution to disperse air bubbles and kept kneaded and cooled. A noodle-like solid was discharged from a punching plate at the outlet. This was cooled and ground to obtain a high-quality crystalline mixture solid containing maltitol. The obtained powders were sifted to obtain powders having a particle size of 16 to 50 mesh which were then used for the measurement of oil absorptivity, bulk density (apparent specific gravity) and melting point. The results are shown in Table 1.

When the inside of the kneader was observed in the course of operation, the kneaded product in the zone right after the supply of the raw material solution contained fine air bubbles uniformly dispersed therein by kneading with the kneader. When this was observed through a microscope, the formation of maltitol crystals was not seen. Further, when the kneaded product in the subsequent zone was observed through a microscope, maltitol crystals were observed.

Example 4

A maltitol aqueous solution (maltitol purity=88.3 wt %, solid content=97.7 wt %, 129° C.) was continuously supplied into a continuous kneader having a slender kneading/cooling zone (KRC kneader S-5 of Kurimoto, Ltd., 28 rpm, jacket temperature=10° C.) at a rate of 100 kg/hr and air was supplied into the kneader by a compressor at the same time to knead the solution by stirring with a kneader puddle while air was contained in the solution to disperse air bubbles and kept kneaded and cooled. A noodle-like solid was discharged from a punching plate at the outlet. This was cooled and ground to obtain a high-quality crystalline mixture solid containing maltitol. The obtained powders were sifted to obtain powders having a particle size of 16 to 50 mesh which was then used for the measurement of oil absorptivity, bulk density (apparent specific gravity) and melting point. The results are shown in Table 1.

TABLE 1

|  | oil absorptivity (%) | bulk density (g/cc) | melting point (° C.) |
| --- | --- | --- | --- |
| powder of Example 1 | 6.8 | 0.72 | 135 |
| powder of Example 3 | 2.7 | 0.75 | 137 |
| powder of Example 4 | 5.4 | 0.77 | 130 |

What is claimed is:

1. A crystalline mixture solid containing maltitol having an oil absorptivity of 0.1 to 6.9 wt % and a bulk density of 0.60 to 0.85 g/cc when it is ground and classified to ensure that at least 70 wt % of the obtained particles should have a particle size of 16 to 50 mesh.

2. The crystalline mixture solid containing maltitol of claim 1 which has a maltitol content of 80 to 99 wt %.

3. The crystalline mixture solid containing maltitol of claim 2 produced by a process comprising dispersing air bubbles in a maltitol aqueous solution, supplying the resulting aqueous solution into a kneader to form a plastic mass and grinding the mass.

4. The crystalline mixture solid containing maltitol of claim 2 produced by a process comprising continuously supplying a maltitol aqueous solution containing air bubbles dispersed therein into an extruder having a slender kneading/cooling zone to knead and cool it to form a maltitol magma and continuously extruding the magma.

5. The crystalline mixture solid containing maltitol of claim 2 produced by a process comprising supplying a maltitol aqueous solution to a kneader, kneading while air is contained in the solution to disperse air bubbles, keeping kneading and cooling the resulting solution to form a plastic mass and grinding the mass.

6. The crystalline mixture solid containing maltitol of claim 2 produced by a process comprising continuously supplying a maltitol aqueous solution into an extruder having a slender cooling/kneading zone, kneading while air is contained in the solution to disperse air bubbles, keeping kneading and cooling the resulting solution to form a maltitol magma and continuously extruding the magma.

7. The crystalline mixture solid containing maltitol of claim 1 produced by a process comprising dispersing air bubbles in a maltitol aqueous solution, supplying the resulting aqueous solution into a kneader to form a plastic mass and grinding the mass.

8. The crystalline mixture solid containing maltitol of claim 1 produced by a process comprising continuously supplying a maltitol aqueous solution containing air bubbles dispersed therein into an extruder having a slender kneading/cooling zone to knead and cool it to form a maltitol magma and continuously extruding the magma.

9. The crystalline mixture solid containing maltitol of claim 1 produced by a process comprising supplying a maltitol aqueous solution to a kneader, kneading while air is contained in the solution to disperse air bubbles, keeping kneading and cooling the resulting solution to form a plastic mass and grinding the mass.

10. The crystalline mixture solid containing maltitol of claim 1 produced by a process comprising continuously supplying a maltitol aqueous solution into an extruder having a slender cooling/kneading zone, kneading while air is contained in the solution to disperse air bubbles, keeping kneading and cooling the resulting solution to form a maltitol magma and continuously extruding the magma.

11. The crystalline mixture solid containing material of claim 1 which has an oil absorptivity of 2.7 to 6.8 wt %.

12. A process for producing a crystalline mixture solid containing maltitol, comprising dispersing air bubbles in a maltitol aqueous solution, supplying the resulting aqueous solution into a kneader to form a plastic mass and grinding the mass.

13. A process for producing a crystalline mixture solid containing maltitol, comprising continuously supplying a maltitol aqueous solution containing air bubbles dispersed therein into an extruder having a slender kneading/cooling zone to knead and cool it to form a maltitol magma and continuously extruding the magma.

14. A process for producing a crystalline mixture solid containing maltitol, comprising supplying a maltitol aqueous solution into a kneader, kneading while air is contained in the solution to disperse air bubbles, keeping kneading and cooling the resulting solution to form a plastic mass and grinding the mass.

15. A process for producing a crystalline mixture solid containing maltitol, comprising continuously supplying a maltitol aqueous solution into an extruder having a slender cooling/kneading zone, kneading while air is contained in the solution to disperse air bubbles, keeping kneading and cooling the resulting solution to form a maltitol magma and continuously extruding the magma.

* * * * *